US00PP12697P2

(12) United States Plant Patent
Geerlings

(10) Patent No.: US PP12,697 P2
(45) Date of Patent: Jun. 11, 2002

(54) ASTRANTIA PLANT NAMED 'SNOW STAR'

(75) Inventor: Aad Geerlings, Lisserbroek (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/639,902

(22) Filed: Aug. 16, 2000

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTITM Computer Database 2001/01, GTI JOUVE Retrieval Software, citation(s) for 'Snow Star' Feb. 6, 2001.*

* cited by examiner

*Primary Examiner*—Bruce R. Campell
*Assistant Examiner*—Annette H. Para
(74) *Attorney, Agent, or Firm*—C. A. Whealy

(57) ABSTRACT

A distinct cultivar of Astrantia plant named 'Snow Star', characterized by its upright plant habit; vigorous growth habit; freely and continuous flowering habit; and large inflorescences with showy involucral bracts that are white with green apices.

2 Drawing Sheets

BACKGROUND OF THE INVENTION

The present Invention relates to a new and distinct cultivar of Astrantia plant, botanically known as *Astrantia involucrata*, and hereinafter referred to by the cultivar name Snow Star.

The new Astrantia is a product of a planned breeding program conducted by the Inventor in Lisserbroek, The Netherlands. The new Astrantia originated from a self-pollination made by the Inventor of unidentified selections of *Astrantia involucrata*. The new Astrantia was selected by the Inventor in 1994 in a controlled environment from the resultant progeny on the basis of its large white inflorescences.

Asexual reproduction of the new cultivar by divisions harvested in Lisserbroek, The Netherlands, has shown that the unique features of this new Astrantia are stable and reproduced true to type in successive generations.

SUMMARY OF THE INVENTION

Plants of the cultivar Snow Star have not been observed under all possible environmental conditions. The phenotype may vary somewhat with variations in environment such as temperature, light intensity, daylength, irrigation amount and frequency, and fertilizer rate without, however, any variance in genotype.

The following traits have been repeatedly observed and are determined to be the unique characteristics of 'Snow Star'. These characteristics in combination distinguish 'Snow Star' as a new and distinct cultivar:

1. Upright plant habit.
2. Vigorous growth habit.
3. Freely and continuous flowering habit.
4. Large inflorescences with showy involucral bracts that are white with green apices.

Plants of the cultivar Snow Star can be compared to plants of the *Astrantia major* cultivar Alba. Plants of the cultivar Snow Star differ from plants of the cultivar Alba in the following characteristics:

1. Plants of the new Astrantia are taller than plants of the cultivar Alba.
2. Plants of the new Astrantia have larger inflorescences than plants of the cultivar Alba.
3. Plants of the new Astrantia flower for a longer period of time than plants of the cultivar Alba.

BRIEF DESCRIPTION OF THE PHOTOGRAPHS

The accompanying colored photographs illustrate the overall appearance of the new Astrantia, showing the colors as true as it is reasonably possible to obtain in colored reproductions of this type. Colors in the photographs may differ slightly from the color values cited in the detailed botanical description which more accurately describe the actual colors of the new Astrantia.

The photograph on the first sheet comprises a side perspective view of a typical flowering plants of 'Snow Star' grown in a container.

The photograph at the top of the second sheet is a close-up view of typical inflorescences of 'Snow Star'.

The photograph at the bottom of the second sheet is a close-up view of a typical inflorescence, a typical leaf and a typical leaf petiole of 'Snow Star'.

DETAILED BOTANICAL DESCRIPTION

In the following description, color references are made to The Royal Horticultural Society Colour Chart except where general terms of ordinary dictionary significance are used. Plants used for the following description were grown in containers under field conditions which closely approximate commercial production conditions during the spring and summer in Lisserbroek, The Netherlands. Plants used for the description were about one year old.

Botanical classification: *Astrantia involucrata* cultivar Snow Star.

Parentage: Self-pollination of unidentified selections of *Astrantia involucrata*, not patented.

Propagation:

*Type cutting.*—By divisions.

*Rooting time.*—Divisions harvested in the spring develop roots in about 30 days at 15 to 20° C.

*Root description.*—Fine.

Plant description:

*Form.*—Upright perennial flowering plant with basal rosette of leaves; numerous erect peduncles support umbels of flowers held well above the foliage. Appropiate for 2-liter containers.

*Crop time.*—About 40 weeks are required to produce finished flowering plants in 2-liter containers.

*Plant height.*—About 80 cm.

*Plant diameter.*—About 50 cm.

*Vigor.*—Vigorous.

*Foliage description.*—Leaves simple, generally symmetrical, palmately-lobed with five lobes, abundant, rosette, convex and long-persisting. Length: About 12 cm. Width: About 18 cm. Shape: Deeply palmately-lobed. Apex: Acute to apiculate. Base: Auriculate. Margin: Doubly serrate to dentate. Texture: Slightly rugose; dull; glabrous. Petiole: Length: About 25 cm. Diameter: About 4 mm. Color: Young foliage, upper surface: 137C to 138A. Young foliage, lower surface: 143A to 143B. Mature foliage, upper surface: 137A to 137B; veins, 139A to 137B. Mature foliage, lower surface: 143A to 143B; veins, 143A to 143B. Petiole color: 143A to 143B.

Inflorescence description:

*Inflorescence/flower appearance.*—Numerous, single, minute, upright, campanulate flowers subtended by showy involucral bracts; flowers arranged in compound umbels. Flowers persistent.

*Quantity of flowers.*—Very freely flowering. During the flowering season, typically about 70 flowers per umbel and about 13 umbels per flowering stem will develop; therefore about 900 flowers per flowering stem and about 15,000 flowers develop per plant. About 40 percent of the flowers are open at any given time during the flowering season.

*Natural flowering season.*—Summer; in the Netherlands, July to September; flowering continuous.

*Fragrance.*—Strong sweet fragrance, unpleasant.

*Flower longevity on the plant.*—About two weeks.

*Inflorescences.*—Diameter: About 4.4 cm. Height: About 4.2 cm. Shape: Hemispherical.

*Flower buds (at showing color).*—Length: About 8 mm. Diameter: About 8 mm. Shape: Obovate. Color: Pale greenish white, 192D, with green, 137D, tones.

*Flowers.*—Length: About 1 cm. Diameter: About 2 mm. Petals: Quantity: Five per flower. Length: About 1 mm. Width: About 0.5 mm. Shape: Elliptic. Apex: Acute. Margin: Entire. Texture: Smooth, dull. Color, both surfaces: 192D or paler than 192D. Involucral bracts: Quantity per inflorescence: About 17. Length: About 2 cm. Width: About 6 mm. Shape: Obovate. Apex: Acute. Margin: Entire. Aspect: Initially upright, then with development, typically horizontal, perpendicular to peduncle. Texture: Smooth. Color, both surfaces: White, close to 157A; apex and veins, green, close to 137A. Calyx: Form: Campanulate; five sepals. Length: About 1.5 mm. Width: About 1.5 mm. Sepal shape: Linear to lanceolate. Sepal apex: Aristate. Sepal margin: Entire. Sepal texture: Smooth, dull. Sepal color, both surfaces: 137C to 137D. Pedicel: Length: About 1 cm. Angle: Erect to about 45° from vertical. Strength: Strong. Color: Close to 65D. Peduncle: Length: About 80 cm. Diameter: About 3.5 mm. Strength: Good, but flexible. Aspect: Mostly upright. Texture: Glabrous; longitudinally ridged. Color: 137C to 138A.

*Reproductive organs.*—Stamens: Quantity: Typically five. Stamen length: About 0.75 mm. Anther shape: Oblong, dorsifixed. Anther length: About 6 mm. Anther width: Less than 4 mm. Anther color: Dark purple brown. Pollen amount: Scarce. Pollen color: 157C to 157D. Pistils: Quantity: Two. Pistil length: About 4 mm. Style length: About 3.5 mm. Style color: 193B. Stigma length: About 0.1 mm. Stigma diameter: About 0.1 mm. Stigma color: 157D. Ovary color: 143A to 143B with pale green, 193B, ribs.

*Fruit description.*—Type: Capsule. Length: About 9 mm. Diameter: About 3 mm. Shape: Elliptic. Color: 199A to 199B.

*Seed description.*—Length: About 4.5 mm. Diameter: About 2 mm. Shape: Elliptic to slightly obovate. Color: 175A.

Disease resistance: Plants of the new Astrantia have been noted to be resistant to pathogens common to Astrantia.

Weather tolerance: Plants of the new Astrantia are tolerant to rain and wind.

It is claimed:

1. A new and distinct cultivar of Astrantia plant named 'Snow Star', as illustrated and described.

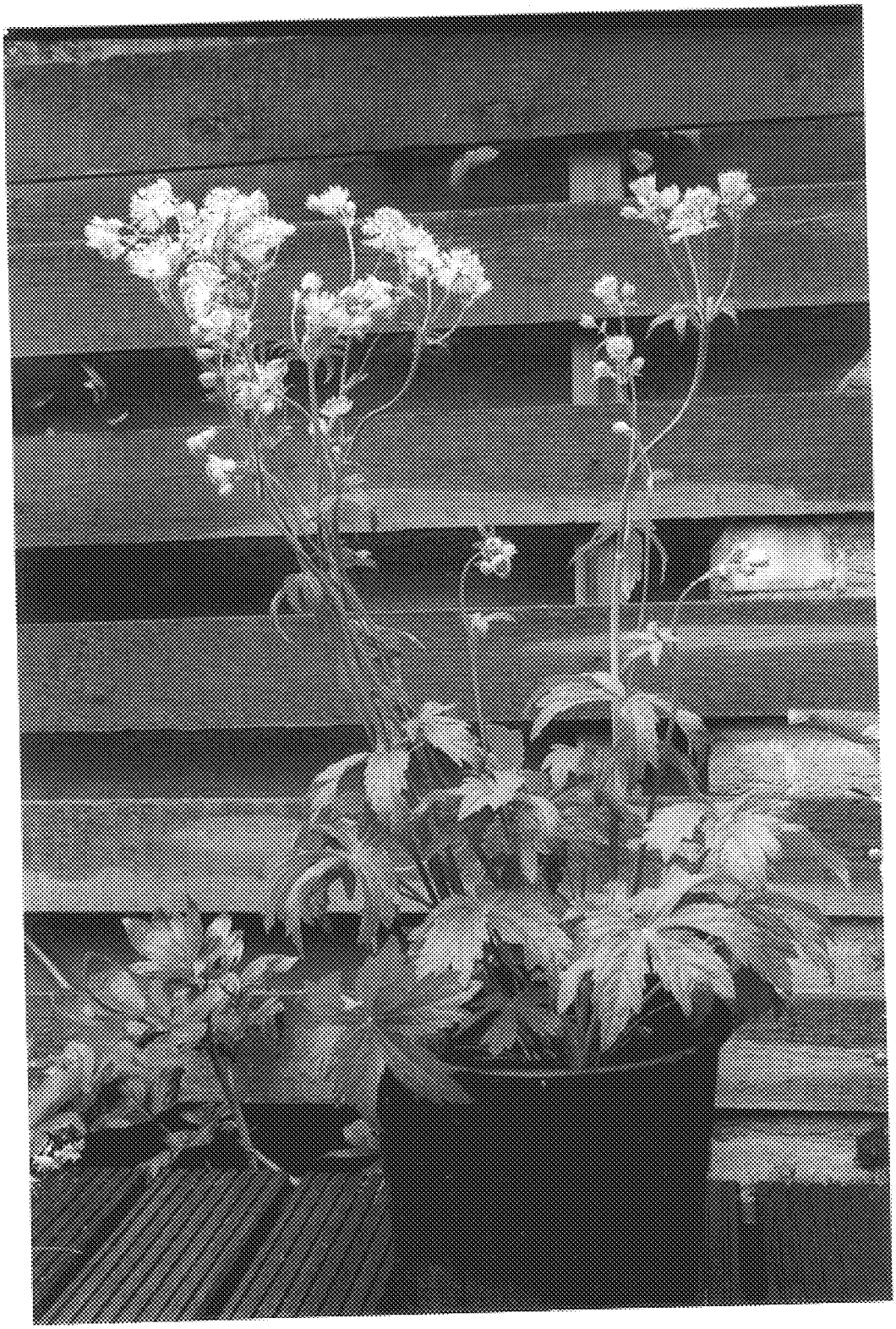

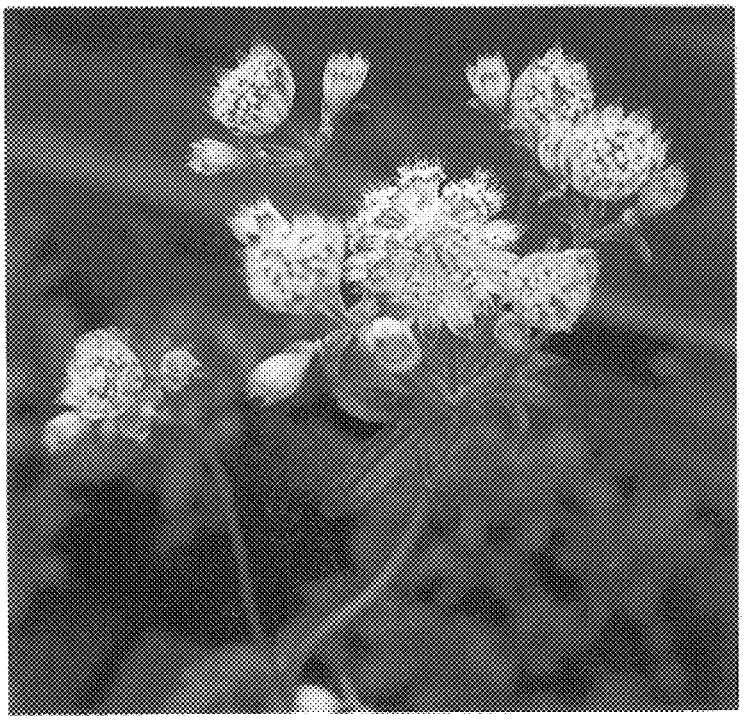
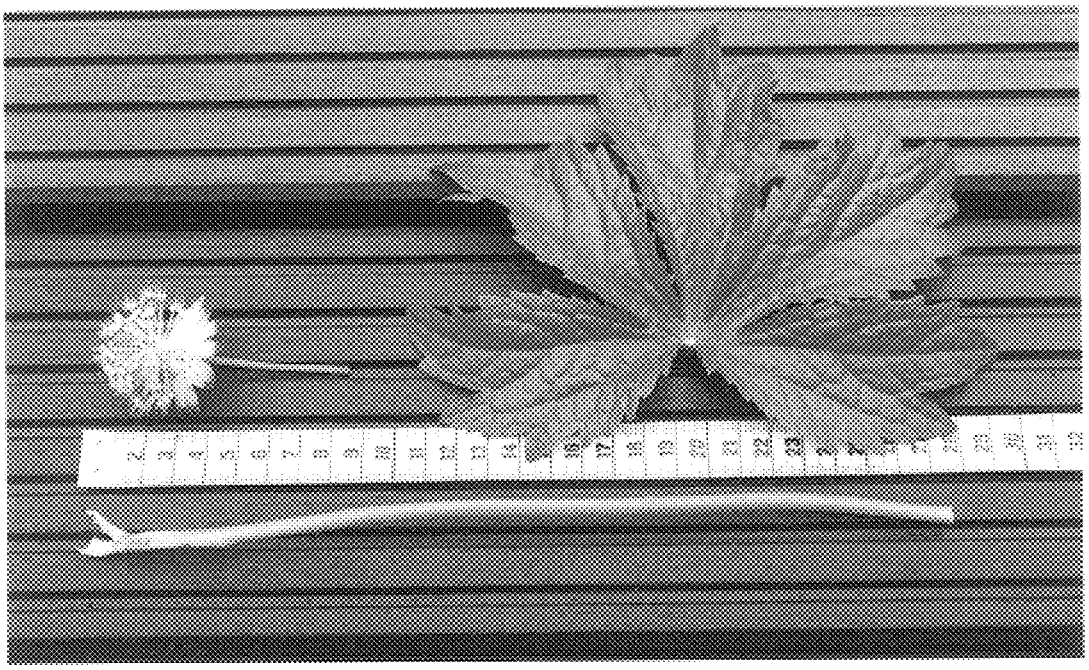

* * * * *